United States Patent
Kameyama

(10) Patent No.: US 6,399,770 B1
(45) Date of Patent: Jun. 4, 2002

(54) PREPARATION OF β-HYDROXY ESTERS USING AMMONIUM BOROHYDRIDES

(75) Inventor: Yutaka Kameyama, Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/555,859

(22) PCT Filed: Oct. 6, 1999

(86) PCT No.: PCT/JP99/05508

§ 371 (c)(1),
(2), (4) Date: Jun. 6, 2000

(87) PCT Pub. No.: WO00/20424

PCT Pub. Date: Apr. 13, 2000

(30) Foreign Application Priority Data

Oct. 7, 1998 (JP) ............................................. 10-284656

(51) Int. Cl.[7] ..................... C07D 501/04; C07B 69/675; C07B 35/02; C07B 41/02
(52) U.S. Cl. ......................... 540/215; 540/222; 560/60; 560/179
(58) Field of Search ................................ 540/215, 222; 560/179, 60

(56) References Cited

U.S. PATENT DOCUMENTS

| 2,852,529 A | 9/1958 | Poos ....................... 260/340.9 |
| 3,989,695 A | 11/1976 | Scartazzini et al. ...... 260/243.8 |
| 4,216,168 A | 8/1980 | Evans et al. ............. 260/567.6 |
| 5,660,711 A | 8/1997 | Walker et al. ............... 205/425 |
| 5,750,682 A | 5/1998 | Sogli et al. .................. 540/215 |
| 6,005,101 A | 12/1999 | Sogli et al. .................. 540/215 |

FOREIGN PATENT DOCUMENTS

| JP | 59-34714 | * 2/1984 |
| JP | 9-504306 | 4/1997 |

OTHER PUBLICATIONS

Sugiura, Chem Abs. 118, 254402 (1992).*

Akita, Tetrahedron: Assymetry 6(9) 2131 (1995).*

Milos Hudlicky: "Reductions in Organic Chemistry", 1984, Ellis Horwod, Chichester, GB; XP002180440, pp 13–22, pp 160–161.

Helvetica Chimica Acta, Verlag Helvetica Chimica Acta. Basel, CH, vol. 57, No. 7, Nov. 06, 1974, pp 1919–1934, XP 000670085, ISSN: 0018–109X.

* cited by examiner

*Primary Examiner*—Mark L. Berch
(74) *Attorney, Agent, or Firm*—Kubovcik & Kubovcik

(57) ABSTRACT

A process for preparing a β-hydroxyester comprising reducing a β-keto ester in the presence of a salt of ammonium borohydride.

3 Claims, No Drawings

PREPARATION OF β-HYDROXY ESTERS USING AMMONIUM BOROHYDRIDES

This application is the National Stage Application of PCT/JP99/05508 filed Oct. 6, 1999.

TECHNICAL FIELD

The present invention relates to a process for preparing a β-hydroxyester.

The β-hydroxyester of the present invention has an active hydroxyl group in the β-position, and is a very important compound in terms of synthetic chemistry. For example, 3-hydroxycepham compound, which can be readily converted to 3-norcephem skeleton, is an important intermediate of ceftizoxime or ceftibutene both widely used as an injection and an oral drug, respectively (Katsuji SAKAI, "Handbook of Latest Antibiotics", 9th ed., pp. 72 and 85, 1994) and is in industrially wide use.

BACKGROUND ART

A β-keto ester is generally unstable under reaction conditions under which hydrolysis tends to occur such as alkaline conditions. The reduction of β-keto ester under such conditions involves various side reactions, thus making it difficult to give the contemplated product.

For example, a 3-ketocepham compound (3-hydroxycephem compound) is unstable under such reaction conditions and, when reacted, gives a reaction product in low yields, so that the reaction should be conducted at an extremely low temperature. Stated more specifically, known methods include those described in JP-B-59-34714 and Pure & Appl. Chem., 59, 1041 (1987) (hereinafter referred to as "Publication 1"). JP-B-59-34714 discloses a method wherein the reaction is carried out in methanol at 0° C. The reproduced method shows that a product is produced in a yield of only 50 to 60%. On the other hand, Publication 1 discloses a method wherein a 3-hydroxycephem compound is dissolved in a solvent mixture of dichloromethane and methanol and the solution is reduced at −60° C. using sodium borohydride. Since the reaction is performed at a low temperature of −60° C., the method is not industrially advantageous.

Publication 1 states that when the reduction is conducted at 0° C., i.e. a temperature commonly employed, a reaction for removal of substituent $R^3$ occurs, resulting in production of the contemplated product in a very low yield. The method of JP-B-59-34714 produces a product in a low yield presumably for the same reason.

Helvetica Chimica Acta 57, 1919 (1974) (hereinafter referred to as "Publication 2") discloses a method in which exomethylene cepham is subjected to ozone decomposition as illustrated below in a scheme, giving a 3-hydroxycephem compound, while ozonide is simultaneously reduced in the same reaction system to produce a 3-hydroxycepham compound. However, the yield of the product is as low as 31.8% which means that the method is not suitable for practical use.

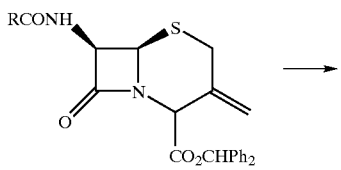

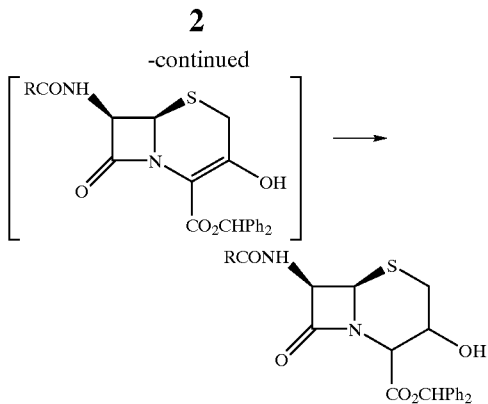

wherein R is benzyl group.

As described above, a practical process has not been established for preparing a β-hydroxyester from a β-keto ester of low stability. Currently there is an urgent need for developing an industrially practical process.

An object of the present invention is to provide a process widely applicable for preparing a β-hydroxyester, the process being free from the drawbacks of conventional processes and capable of giving the contemplated β-hydroxyester in a high yield and with a high purity.

DISCLOSURE OF THE INVENTION

The present invention provides a process for preparing a β-hydroxyester comprising reducing a β-keto ester in the presence of a salt of ammonium borohydride.

In an attempt to develop the process for preparing a β-hydroxyester, the present inventor directed attention to the fact that the β-hydroxyester or β-keto ester shows a very unstable behavior in reduction under alkaline conditions.

It is known that reduction at a relatively high temperature (e.g. approximately 0° C.) entails side reactions such as hydrolysis, thus giving the contemplated compound in a lower yield and with a lower purity. For example, the reaction of Publication 1 produces $(C_6H_5)_2CHOH$ as a by-product. Publication 1 explains that the by-product is produced due to the attack by hydride when the reaction temperature is elevated to approximately 0° C.

Considering that the by-product is produced due to a high basicity derived from sodium borohydride or due to a great hydride-reducing capability of sodium borohydride, the present inventor attempted to find out a salt of borohydride which does not increase the basicity in the reaction system and which is capable of selectively reducing a β-keto ester or its ketoenol isomer.

It is already known to produce a salt of borohydride such as aluminum, lithium or zinc salt in the reaction system for use in the reduction. However, such salt failed to achieve the contemplated object. On the other hand, a salt of ammonium borohydride has not been heretofore used for this purpose and was proposed as a useful reagent for the first time in this invention. It was discovered that the foregoing reduction advantageously proceeds in the presence of a salt of ammonium borohydride, giving the contemplated β-hydroxyester in a high yield and with a high purity. Further, no by-product was produced even when the reaction temperature was raised to 0° C.

In the present invention, a β-hydroxyester is prepared by reduction of β-keto ester in the presence of a salt of ammonium borohydride.

The β-keto ester for use as the starting material in the process of the present invention is not limited and includes conventional compounds. Among useful β-keto esters, preferred are 3-keto cepham compound represented by the formula (1) and 3-hydroxycephem compound represented by the formula (1') which is the keto-enol isomer of the 3-keto cepham compound

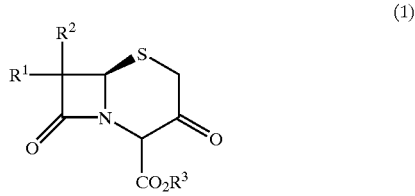
(1)

wherein $R^1$ is hydrogen atom, halogen atom, amino group, protected amino group or a group —N=CH—Ar (in which Ar is phenyl group optionally having a substituent), $R^2$ is lower alkyl group optionally having hydroxyl group or protected hydroxyl group as a substituent, hydrogen atom, halogen atom, lower alkoxy group, lower acyl group, hydroxyl group or protected hydroxyl group, and $R^3$ is hydrogen atom or carboxylic acid-protecting group

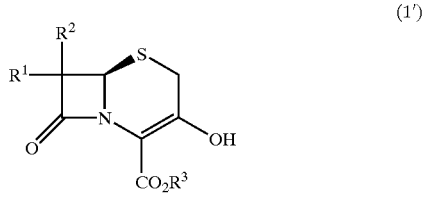
(1')

wherein $R^1$, $R^2$ and $R^3$ are as defined above.

Examples of the groups described in the present specification are as follows unless they are otherwise specified:

Halogen atom means fluorine, chlorine, bromine, iodine, or the like. Lower alkyl group means, for example, a straight-chain or branched alkyl groups having 1 to 4 carbon atoms such as methyl, ethyl, n-propyl, isopropyl, n-butyl, isobutyl, sec-butyl and tert-butyl. Examples of the lower alkoxy groups are straight-chain or branched alkoxy groups having 1 to 4 carbon atoms such as methoxy, ethoxy, n-propoxy, isopropoxy, n-butoxy, isobutoxy, sec-butoxy and tert-butoxy.

Examples of the protected amino group represented by $R^1$ are phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-t-butylbenzamido, p-methoxybenzamido, p-chlorobenzamido, p-bromobenzamido, etc. In addition to these, there are the groups disclosed in "Protective Groups in Organic Synthesis written by Theodora W. Greene, 1981, by John Wiley & Sons. Inc." (hereinafter referred to as the "Publication 3"), Chap. 7 (pp. 218–287), and phenylglycylamido, phenylglycylamido in which amino group is protected, p-hydroxyphenylglycylamido, and p-hydroxyphenylglycylamido in which either of amino and hydroxyl, or both of these are protected. Examples of protective groups for the amino of phenylglycylamido group and p-hydroxyphenylglycylamido group are those disclosed in the Publication 3, Chap. 7 (pp. 218–287). Examples of protective groups for the hydroxyl of p-hydroxyphenylglycylamido are those disclosed in the Publication 3, Chap. 2 (pp. 10–72).

Examples of phenyl groups represented by Ar in —N=CH—Ar group defined by $R^1$ are phenyl and phenyl groups such as p-methoxyphenyl, p-nitrophenyl and m-hydroxyphenyl which may have a substituent including lower alkoxyl group, nitro, hydroxyl or the like.

Examples of the lower acyl represented by $R^2$ are straight-chain or branched acyl groups having 1 to 4 carbon atoms such as formyl, acetyl, propionyl, butyryl and isobutyryl.

Examples of protected hydroxyl groups for lower alkyl represented by $R^2$ and substituted with hydroxyl group or protected hydroxyl group, and examples of protective groups for the protected hydroxyl represented by $R^2$, are those disclosed in the Publication 3, Chap. 2 (pp. 10–72). The above lower alkyl groups represented by $R^2$ is substituted by substituents of the same or different kinds selected from among hydroxyl group and the protected hydroxyl groups as defined above, and at least one of such substituents may be substituted in the same or different carbon.

Exemplary of the carboxylic acid protecting groups represented by $R^3$ are benzyl, p-methoxybenzyl, p-nitrobenzyl, diphenylmethyl, trichloroethyl, tert-butyl, or the groups described in the Publication 3, Chap. 5 (pp. 152–192).

3-Keto cepham compound (1) and its keto-enol isomer (1') can be prepared according to the method disclosed in the Publication 1 as shown in the reaction scheme below. In the scheme, Me stands for methyl, Ph for phenyl, Ts for tosyl and Py for pyridyl.

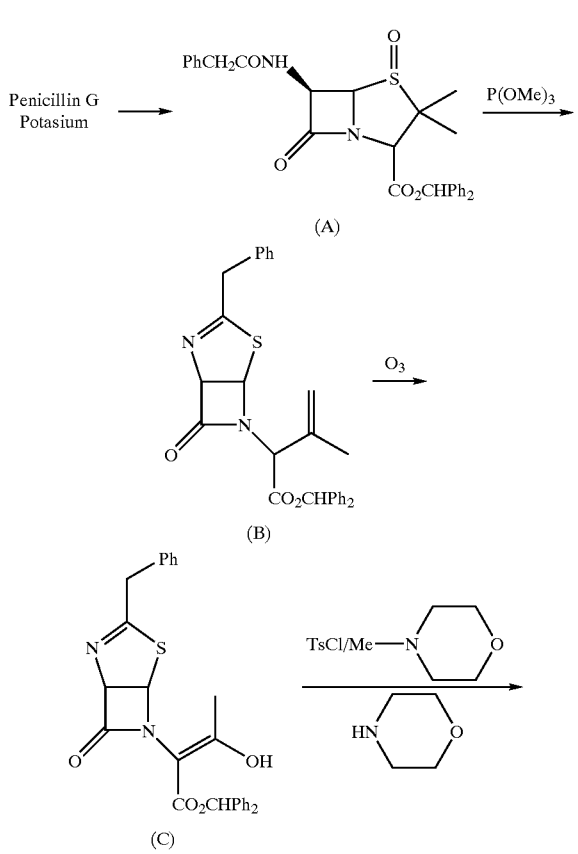

-continued

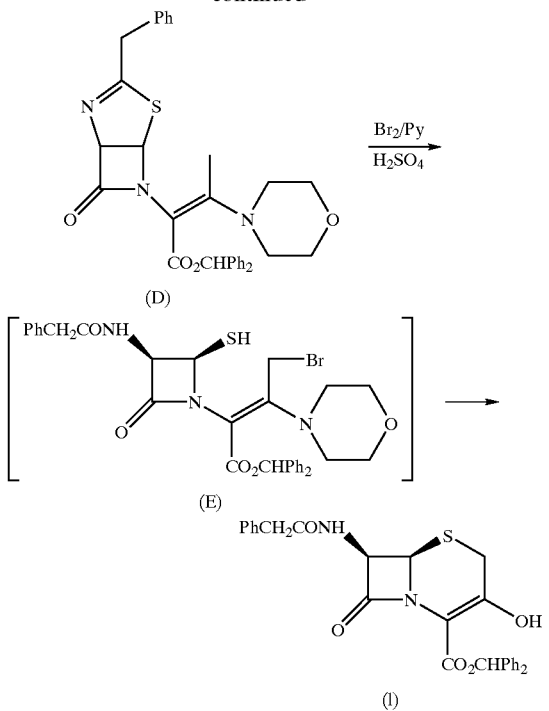

When 3-keto cepham compound (1) or its keto-enol isomer (1') is used as the starting material in the present invention, 3-hydroxycepham compound represented by the formula (2) can be prepared in a high yield and with a high purity

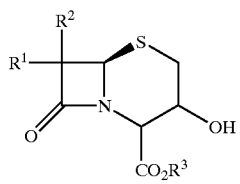

wherein $R^1$, $R^2$ and $R^3$ are as defined above.

The salt of ammonium borohydride for use in the present invention includes not only ammonium borohydride but tetramethylammonium borohydride, tetraethylammonium borohydride, tetra-n-propylammonium borohydride, tetra-n-butylammonium borohydride and like tetraalkylammonium borohydrides. The amount of a salt of ammonium borohydride to be used in the invention is not specifically limited and is such that the β-keto ester used as the starting material is completely exhausted. The amount is usually about 1 to about 10 moles, preferably about 1 to about 3 moles, per mole of β-keto ester used.

In the present invention, it is possible to use a salt of ammonium borohydride prepared in the reaction system. The salt of ammonium borohydride can be produced by the presence of alkali metal salt of borohydride and ammonium salt in the reaction system. Examples of alkali metal salts of borohydride are sodium borohydride and potassium borohydride. The alkali metal salts of borohydride can be used either alone or in combination. The amount of alkali metal salt of borohydride to be used in the invention is not specifically limited and is such that the β-keto ester used as the starting material is completely exhausted due to the salt of ammonium borohydride produced by the reaction of alkali metal salt of borohydride with ammonium salt. The amount is usually about 1 to about 10 moles, preferably about 1 to about 3 moles, per mole of β-keto ester used.

Useful ammonium salts are, for example, ammonium chloride, ammonium bromide, ammonium iodide, tetraethylammonium chloride, tetrabutylammonium bromide and like halogenated ammonium salts, ammonium perchlorate, tetraethylammonium perchlorate, tetrabutylammonium perchlorate and like salts of ammonium perchlorate, tetrabutylammonium tosylate and like salts of ammonium sulfonate, tetraethylammonium borofluoride, tetrabutylammonium borofluoride and like salts of ammonium borofluorides. Among them, halogenated ammonium salts are preferably usable. Ammonium salts can be used either alone or in combination. The amount of ammonium salt to be used is not specifically limited and can be suitably selected from a wide range. The amount is usually about 0.01 to about 5 kg, preferably about 0.1 to about 2 kg, per kilogram of β-keto ester used.

The reduction of the present invention is usually carried out in a solvent. Useful solvents are, for example, methanol, ethanol, propanol, n-butanol and like straight-chain lower alkyl alcohols, 2-propanol, 2-butanol, tert-butanol and like branched-chain lower alkyl alcohols, ethylene glycol, propylene glycol and like dihydric alcohols, diethyl ether, ethyl propyl ether, ethyl butyl ether, dipropyl ether, diisopropyl ether, dibutyl ether, methyl cellosolve, dimethoxyethane, diglyme, triglyme and like ethers, tetrahydrofuran, dioxane, dioxolan and like cyclic ethers, acetonitrile, propionitrile, butyronitrile, isobutyronitrile, valeronitrile and like nitriles, benzene, toluene, xylene, chlorobenzene, anisole and like substituted or unsubstituted aromatic hydrocarbons, dichloromethane, chloroform, dichloroethane, trichloroethane, dibromoethane, propylene dichloride, carbon tetrachloride and like halogenated hydrocarbons, pentane, hexane, heptane, octane and like aliphatic hydrocarbons, cyclopentane, cyclohexane, cycloheptane, cyclooctane and like cycloalkanes.

These solvents can be used either alone or in combination. Among them, preferred solvents are straight-chain lower alkyl alcohols and solvent mixtures of such alcohols and other solvents. These solvents may contain water, when so required. The amount of the solvent to be used is not specifically limited but is usually about 2 to about 200 liters, preferably about 5 to about 50 liters, per kilogram of β-keto ester used.

The reaction according to the invention is conducted at a temperature of about −78 to about +150° C., preferably about −30 to about +50° C. and is completed at the same time as the completion of mixing of starting compounds or about 10 hours or less after mixing.

When the obtained product is an unstable compound in the present invention, it is possible, when required, to inactivate the salt of ammonium borohydride remaining in the reaction system after completion of the reaction. The inactivation can be done by addition of an inorganic acid such as hydrochloric acid, nitric acid or sulfuric acid to the reaction system.

The desired product obtained by the reaction of the invention, i.e. 3-hdroxycepham compound, can be easily isolated and purified from the reaction system by conventional means.

BEST MODE OF CARRYING OUT THE INVENTION

The present invention is described in detail with reference to the following examples and comparative examples.

EXAMPLE 1

One gram of compound (1a) (compound represented by the formula (1) wherein $R^1$=PhCH$_2$CONH, $R^2$=H and $R^3$=CH$_2$C$_6$H$_4$-p-OCH$_3$) and 0.5 g of ammonium chloride were weighed out and placed into a 300-ml 4-necked flask, followed by addition of 10 ml of methanol. The mixture were stirred to obtain a solution. The solution was cooled to 0° C. and 0.11 g of sodium borohydride was gradually added. The progress of the reaction was monitored by high performance liquid chromatography (HPLC). After confirming whether the compound (1a) used as the starting compound was completely exhausted, 5 ml of 1N hydrochloric acid was added, thereby inactivating the remaining ammonium borohydride and simultaneously crystallizing the reaction product. The obtained crystals were separated from the slurry by filtration under reduced pressure, washed with isopropanol containing 33% water and dried under reduced pressure to give 0.91 g (yield 91%) of the contemplated compound (2a) (compound of the formula (2) wherein $R^1$, $R^2$ and $R^3$ are as defined above).

1H-NMR(DMSO-d$_6$) δ 2.70(dd, J=3.6, 13.2 Hz, 1H), 3.09(dd, J=10.5, 13.2 Hz, 1H), 3.50 (d, J=13.0 Hz, 1H), 3.54(d, J=13.0 Hz, 1H), 3.73(s, 3H), 3.91(m, 1H), 4.56(d, J=6.0 Hz, 1H), 5.04(d, J=4.1 Hz, 1H), 5.05(d, J=12.1 Hz, 1H), 5.10(d, J=12.1 Hz, 1H), 5.33(dd, J=4.1, 8.2 Hz, 1H), 5.99(d, J=4.2 Hz, 1H), 6.88–7.37(m, 9H), 9.06(d, J=8.2 Hz, 1H).

COMPARATIVE EXAMPLE 1

The reaction was carried out in the same manner as in Example 1 with the exception of not using ammonium chloride, giving only 0.32 g (yield 32%) of the contemplated compound (2a).

EXAMPLES 2 to 10

The reaction was carried out in the same manner as in Example 1 with the exception of replacing the solvents with those shown in Table 1. Table 1 also indicates the yields of the contemplated compound (2a).

TABLE 1

| Example | solvent (ml) | yield (%) |
| --- | --- | --- |
| 2 | CH$_2$Cl$_2$ (5)/methanol (5) | 86 |
| 3 | ethanol (10) | 88 |
| 4 | CH$_2$Cl$_2$ (5)/2-propanol (5) | 81 |
| 5 | tetrahydrofuran (10) | 78 |
| 6 | tetrahydrofuran (5)/methanol (5) | 86 |
| 7 | tetrahydrofuran (5)/ethanol (5) | 85 |
| 8 | dioxane (5)/methanol (5) | 83 |
| 9 | acetonitrile (10) | 79 |
| 10 | acetonitrile (5)/methanol (5) | 85 |

EXAMPLES 11 to 15

The reaction was carried out in the same manner as in Example 1 with the exception of changing the reaction temperatures to those shown in Table 2. Table 2 also indicates the yields of the contemplated compound (2a).

TABLE 2

| Example | reaction temperature (° C.) | yield (%) |
| --- | --- | --- |
| 11 | −60 ~ −50 | 98 |
| 12 | −30 ~ −25 | 95 |
| 13 | −5 ~ −10 | 92 |

TABLE 2-continued

| Example | reaction temperature (° C.) | yield (%) |
| --- | --- | --- |
| 14 | 10 ~ 25 | 88 |
| 15 | 25 ~ 30 | 82 |

EXAMPLES 16 to 20

The reaction was carried out in the same manner as in Example 1 with the exception of changing the amount of ammonium chloride used to that shown in Table 3. Table 3 also indicates the yields of the contemplated compound (2a).

TABLE 3

| Example | amount of ammonium chloride (g) | yield (%) |
| --- | --- | --- |
| 16 | 0.1 | 82 |
| 17 | 0.25 | 90 |
| 18 | 0.75 | 91 |
| 19 | 1.0 | 92 |
| 20 | 2.0 | 91 |

EXAMPLES 21 to 24

The reaction was carried out in the same manner as in Example 1 with the exception of replacing the ammonium chloride with other ammonium salts shown in Table 4. Table 4 also indicates the yields of the contemplated compound (2a).

TABLE 4

| Example | ammonium salt (g) | yield (%) |
| --- | --- | --- |
| 21 | tetraethylammonium chloride | 86 |
| 22 | tetrabutylammonium bromide | 80 |
| 23 | tetraethylammonium p-toluenesulfonate | 72 |
| 24 | tetrabuthylammonium tetrafluoroborate | 80 |

EXAMPLES 25 to 29

The reaction was carried out in the same manner as in Example 1 with the exception of changing the amount of methanol to that shown in Table 5. Table 5 also indicates the yields of the contemplated compound (2a).

TABLE 5

| Example | amount of methanol (ml) | yield (%) |
| --- | --- | --- |
| 25 | 5 | 87 |
| 26 | 20 | 92 |
| 27 | 40 | 92 |
| 28 | 50 | 91 |
| 29 | 100 | 92 |

EXAMPLE 30

A 250 g quantity of compound (1b) (compound represented by the formula (1) wherein $R^1$=PhCH$_2$CONH, $R^2$=H and $R^3$=CHPh$_2$) and 125 g of ammonium chloride were weighed out and placed into a 5000-ml 4-necked flask, followed by addition of 2500 ml of methanol. The mixture was stirred to obtain a solution. The solution was cooled to 0° C. and 25 g of sodium borohydride was gradually added. The progress of the reaction was monitored by HPLC. After confirming whether the compound (1a) used as the starting compound was completely exhausted, 1250 ml of 1N hydrochloric acid was added, thereby inactivating the remaining ammonium borohydride and simultaneously crystallizing the reaction product. The crystals were separated from the slurry by filtration under reduced pressure, washed with isopropanol containing 33% water and dried under reduced pressure to give 225 g (yield 90%) of the contemplated compound (2b) (compound of the formula (2) wherein $R^1$, $R^2$ and $R^3$ are as defined above).

1H-NMR(DMSO-$d_6$) δ 2.73(dd, J=3.3, 13.2 Hz, 1H), 3.08(dd, J=10.5, 13.2 Hz, 1H), 3.42(d, J=13.8 Hz, 1H), 3.55(d, J=13.8 Hz, 1H), 4.01(m, 3H), 4.71(d, J=6.3 Hz, 1H), 5.08(d, J=3.9 Hz, 1H), 5.37(dd, J=3.9, 8.1 Hz, 1H), 6.09(d, J=4.2 Hz, 1H), 6.83(s, 1H), 7.20–7.42(m, 15H), 9.07(d, J=8.1 Hz, 1H).

EXAMPLE 31

A 10 g quantity of methyl acetoacetate ($CH_3COCH_2COOCH_3$) and 25 g of ammonium chloride were weighed out and placed into a 300-ml 4-necked flask, followed by addition of 100 ml of methanol. The mixture was stirred to obtain a solution. The solution was cooled to 0 to 3° C. and 4.6 g of sodium borohydride was gradually added. After addition of sodium borohydride, stirring was conducted at the same temperature for 30 minutes. A 100 ml quantity of 1N hydrochloric acid was added to the mixture and extraction was performed with 200 ml of ethyl acetate and 200 ml of water. The ethyl acetate layer was washed with 100 ml of 2% aqueous solution of sodium bicarbonate. Then the mixture was dried over anhydrous sodium sulfate and was concentrated under reduced pressure, giving 5.6 g (yield 51%) of the desired methyl ester of 3-hydroxybutanoic acid [$CH_3CH(OH)CH_2COOCH_3$].

1H-NMR(CDCl$_3$) δ 1.21(d, J=6.3 Hz, 1H), 2.39(dd, J=8.1, 16.5 Hz, 1H), 2.49(dd, J=4.2, 16.5 Hz, 1H), 2.89(d, J=3.6 Hz, 1H), 3.70(s, 3H), 4.19(m, 1H).

COMPARATIVE EXAMPLE 2

The reaction was carried out in the same manner as in Example 31 with the exception of not using ammonium chloride, but failed to give the desired methyl ester of 3-hydroxybutanoic acid.

INDUSTRIAL APPLICABILITY

According to the present invention, the contemplated β-hydroxyester can be prepared by a practical process in a high yield and with a high purity.

I claim:

1. A process for preparing a β-hydroxyester of the formula (2)

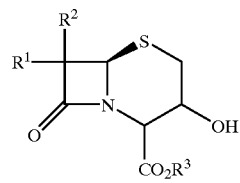

comprising reducing a 3-keto cepham compound represented by the formula (1) or a 3-hydroxycephem compound represented by the formula (1') which is the keto-enol isomer of the 3-keto cepham compound

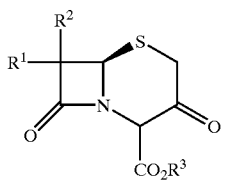

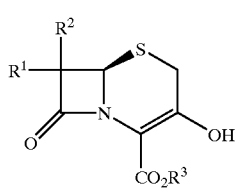

wherein $R^1$ is hydrogen atom, halogen atom, amino group, protected amino group or a group —N=CH—Ar (in which Ar is phenyl group optionally having a substituent selected from the group consisting of lower alkoxyl, nitro and hydroxyl), $R^2$ is lower alkyl group optionally having a hydroxyl group or protected hydroxyl group as a substituent, hydrogen atom, halogen atom, lower alkoxy group, RC(O)—, where R is straight-chain or branched lower alkyl, hydroxyl group or protected hydroxyl group, and $R^3$ is hydrogen atom or carboxylic acid-protecting group, in the presence of a salt selected from the group consisting of ammonium borohydride and tetraalkylammonium borohydride.

2. A process as defined in claim 1 wherein said salt is used in an amount of 1 to 10 moles per mole of β-keto ester.

3. A process as defined in claim 1 wherein said salt is produced by the reaction of alkali metal salt of borohydride and quaternary ammonium salt in the reaction system.

* * * * *